United States Patent [19]
Ruksenas et al.

[11] Patent Number: 5,583,044
[45] Date of Patent: Dec. 10, 1996

[54] FLUID SAMPLER AND TESTING UNIT

[76] Inventors: M. A. Ruksenas, 1123 E. Mission, Fallbrook, Calif. 92028; Robert Mancuso, 870 Seabright La., Solana Beach, Calif. 92075

[21] Appl. No.: 74,557

[22] Filed: Jun. 11, 1993

[51] Int. Cl.⁶ .................................................. C12M 1/34
[52] U.S. Cl. .................... 435/287.5; 435/288.2; 435/304.2; 422/102
[58] Field of Search .................... 435/29, 30, 31, 435/34, 291, 292, 294, 296, 299, 300, 807, 808, 810, 287.1, 287.5, 288.1, 288.2, 288.7, 300.1, 304.1, 304.2, 307.1; 422/58, 59, 61, 83, 92, 99, 102; 73/19.01, 19.05, 864.51, 864.91

[56] References Cited

U.S. PATENT DOCUMENTS

| | | | |
|---|---|---|---|
| 1,834,536 | 12/1931 | Schaut | 435/291 |
| 4,314,029 | 2/1982 | Ohtake et al. | 435/291 |
| 4,868,110 | 9/1989 | DesRosier et al. | 435/34 |
| 4,952,498 | 8/1990 | Waters | 435/34 |
| 5,047,331 | 9/1991 | Swaine et al. | 435/34 |

FOREIGN PATENT DOCUMENTS 2102947  2/1983  United Kingdom ............ 435/34

*Primary Examiner*—William H. Beisner

[57] ABSTRACT

A sampling and testing unit or bottle and method to perform presumptive testing of aqueous solutions to determine bacterial contamination if present, such testing to measure and indicate the presence of contaminants which, if in the presence of nutrients, will multiply in such a manner as to form gaseous products such as those which would be formed if the growth of same were to be a fermentation reaction with the evolution of gaseous material which would be easily observed by the positive displacement of the aqueous solution from an inverted tube or tubes incorporated into the body of the apparatus, in addition to the brilliant chromophoric confirmations tests as would be established by indicator color changes of materials incorporated in the nutrient media placed in the apparatus.

8 Claims, 1 Drawing Sheet

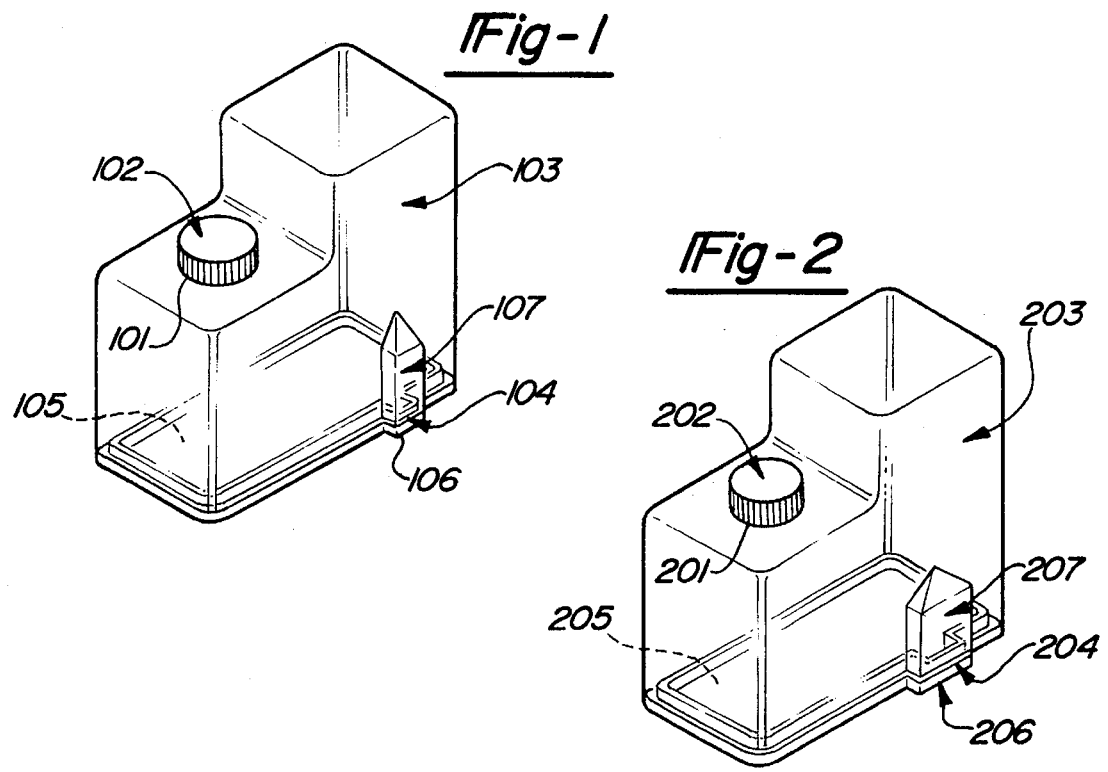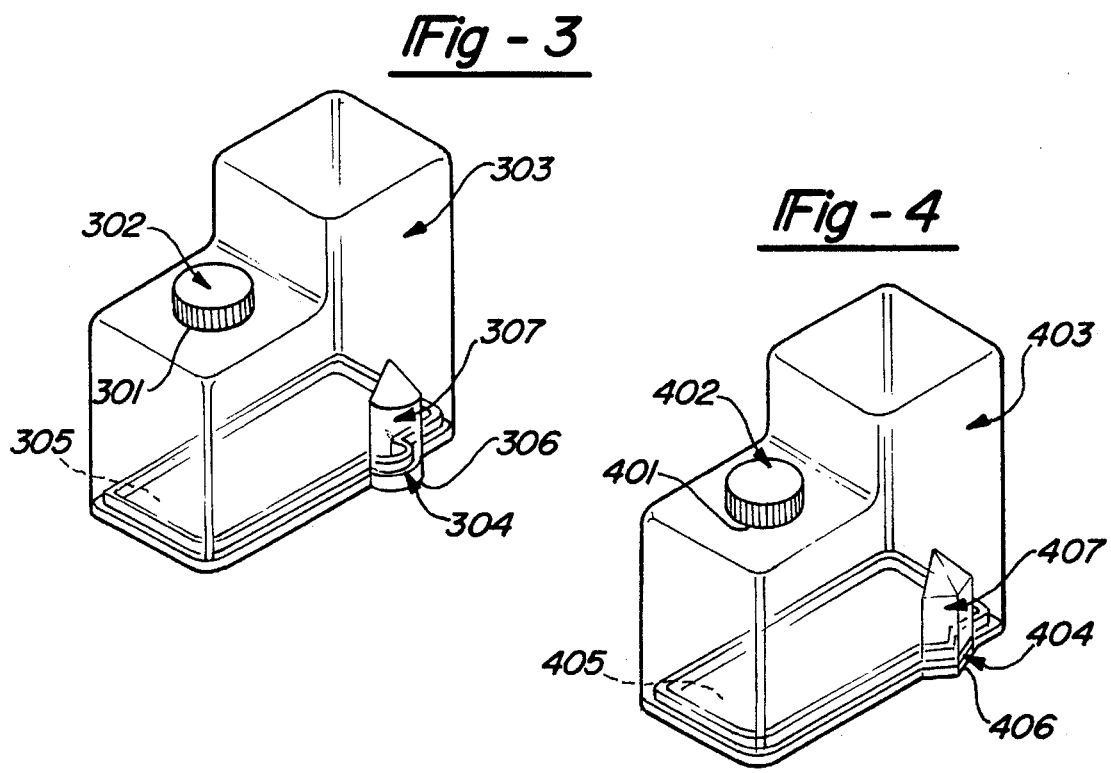

5,583,044

FLUID SAMPLER AND TESTING UNIT

BACKGROUND OF THE INVENTION

1. Field of the Invention

The invention relates to an apparatus and method for sampling and testing bacterial contamination of aqueous fluids or solutions.

2. Description of the Prior Art

Apparatii or combinations thereof are known for testing of bacterial contaminated aqueous solutions when gaseous substances are formed during the growth of the contaminant such as encountered during fermentation growth or reactions. Most of the methods used are composites of methods quickly put together or assembled to merely illustrate a point. One method of determining the positive growth is that of the observation of pressure build-up with the testing containment vessel. This method if not properly monitored or pressure release controlled can lead to such high pressure build-up as to cause destruction of the containment vessel through explosion.

A second method of monitoring such a positive growth pattern is to contain and duct the gaseous evolution into a second container or vessel containing an aqueous media and observe bubble formation as a result of the out-gassing, also acting as a positive pressure control device. This method has been used extensively to prevent the further contamination through back-pressure of the original solution whose growth pattern is being observed or monitored. A modification of this procedure is the use of chemical additives in the second container or vessel to aid in the determination of the type of gaseous material being evolved. Such evolution is observed by the opacity or the color change or both in the second container. Such a change can be a presumptive test for the type or the nature of the gaseous evolution.

An alternative method of determining and observing this positive growth formation has been used extensively. This method incorporates that of filling a second container, e.g., a test tube of appropriate size and shape, with the same nutrient solution used to aid growth and placing it within the original container or vessel. The placement of the second container must be such in conjunction with the original container that it will remain inverted and mechanically filled with the nutrient solution if no bacterial contamination were to exist. Only growth of the bacteria or contaminant would cause or result in the positive displacement of the aqueous solution from the second container. This displacement would be observable and easily discerned. A difficulty with this method often arises due to poorly matched containers which do not remain in the proper original position. This poor matching of vessels can permit the change of position of the inverted tube and permit displacement of the fluid or allow continual refilling of the displaced space resulting in false tests in both instances. Such results require the need for extensive repetitive testing, loss of samples and unnecessary costly expenses.

SUMMARY OF THE PRESENT INVENTION

The present invention incorporates within the growth containment vessel a gaseous pressure plenum which aids in control of the volume of aqueous material which is placed in the container. It permits the repetitive reproducible constant volume sample testing required of both the sampling procedure and growth testing. The pressure plenum serves a second function by acting as a repository or depository chamber for the growth and indicator media which is to be placed within the container vessel prior to final assembly of the apparatus. This embodiment of the tube configuration by its permanency eliminates any possibility of position change or movement, which would be possible with a freely placed tube or container within a container, resulting in false test results. This would be called or classified as a positive presumptive test by the used of such an apparatus. The absolute confidence of the user, scientist or technician would be one more aspect of the efficiency of the test procedure used. The result would be one less degree of freedom of error which would be present in the testing procedures or methods currently used. This confidence as well as the reproducibility of the apparatus and results obtained would aid in the assurance that uniform sampling, testing and results could be compared and universally relatable where ever the apparatus and methods are used.

An additional object of the invention is to permit an inverted tube test means of a variety of geometrical cross sections for facilitating ease of viewing of the results therefore lessening the error of reading test results.

An additional object of the invention is to provide a sampling and testing apparatus which can be constructed inexpensively with equal accuracy from a choice of a variety of materials.

Additional objects of the invention will be clarified or become apparent with the description and drawings to follow.

BRIEF DESCRIPTION OF THE DRAWINGS

FIG. 1 is a schematic view of the apparatus illustrating the preferred embodiment of a square inverted indicator tube configuration.

FIG. 2 is a schematic view of the apparatus with an alternate embodiment of an inverted tube with an oblong configuration.

FIG. 3 is a schematic view of the apparatus with an alternate embodiment of an inverted indicator tube with a semi-circular configuration.

FIG. 4 is a schematic view of the apparatus with an alternate embodiment of an inverted indicator tube with a triangular configuration.

DESCRIPTION OF THE PREFERRED EMBODIMENTS

Positive displacement of the fluid in the rigidly placed inverted indicator tube within the body of the apparatus is achieved with the gaseous evolution resulting from growth of bacteria in the sample placed into the apparatus which has had nutrient incorporated in the apparatus and the entire apparatus is placed in a controlled atmosphere for incubation purposes. The apparatus utilizing present standard methods of analysis for Coliforms assures that a constant reproducible sample size is used consistently and repeatedly to measure a known volume. Repeated use of the same piece of equipment for sample sizing if not used correctly can result in direct contamination as well as cross contamination.

The invention or apparatus with the foregoing characteristics is described in greater detail through reference to the attached drawings.

As shown in FIG. 1, the sample is placed into the apparatus through the circular port 101. The port following sampling of the fluid into the apparatus is capped with a cap, 102, to assure containment of the sample but permit outgassing if a contaminated sample permits growth and the evolution of gaseous materials. The combined volume pressure plenum, 103, aids in assuring that a constant volume sample is achieved each time a like apparatus is used. The inverted indicator tube body, 104, is a contiguous portion of the entire chamber of the apparatus. The base of the apparatus, 105, when assembled to the main body of the apparatus must conform to and be an integral part of the completed final apparatus as it would be for analysis purposes. Item 106, is that of a square tube outer lip of the inverted tube.

FIGS. 2, 3 and 4 are identical in all respects to FIG. 1 with one exception in each. This difference relates to the dimensional geometry of the body of the tube, an integral part of the apparatus. FIG. 2, tube body 204 and inverted lip 206 is that of a rectangular configuration which would afford a larger more visible surface area. FIG. 3, tube body 304 and inverted lip 306 is that of a rounded geometrical configuration and could permit a slightly more visible aqueous displacement by positive gaseous pressure. FIG. 4, tube body 404 and lip 406 of a triangular geometrical configuration could aid in better visual viewing of the aqueous media by positive gaseous displacement. All inverted tubular configurations in each, FIG. 1 through FIG. 4, identified as 107, 207, 307, and 407 are intimately interconnected within each apparatus through the open space port as illustrated. Such opening permits continual and intimate mixing of the samples and media in both the principle chamber and the inverted tube of the apparatus at all times.

The accompanying drawings should be for interpretive purposes only and not be limiting in any manner as the present invention is subject to modification and variations in detail but not in basic concept.

We claim:

1. A fluid sampling and test unit comprising:
   a) a containment chamber defined by a top wall, a bottom wall and at least one side wall, said containment chamber including a pressure plenum chamber defined by a portion of said top wall and said at least one side wall, said top wall including a port positioned thereon, said top wall and said at least one side wall being configured such that at least part of said pressure plenum chamber is located at an elevation above that of said port and such that a constant volume of sample is introduced into said containment chamber each time said unit is used; and
   b) a test chamber having a volume which is less than the volume of said containment chamber, said test chamber being configured such that said at least one side wall defines a portion of said test chamber and such that said test chamber is completely filled with liquid when the constant volume of sample is introduced into said containment chamber, said test chamber communicating with said containment chamber at a level below that of the constant volume of sample such that pressure can be equalized between said containment chamber and said test chamber.

2. The fluid sampling and testing unit of claim 1, wherein said containment chamber and said test chamber are composed of transparent materials.

3. The fluid sampling and testing unit of claim 1, wherein the interior of said containment chamber and said test chamber are clearly visible and observable.

4. The fluid sampling and testing unit of claim 1, wherein said test chamber is in the form of an inverted tube having various geometrical cross sectional configurations.

5. The fluid sampling and testing unit of claim 4, wherein said inverted tube has a square cross sectional configuration.

6. The fluid sampling and testing unit of claim 4, wherein said inverted tube has a rectangular cross sectional configuration.

7. The fluid sampling and testing unit of claim 4, wherein said inverted tube has a semi-circular cross sectional configuration.

8. The fluid sampling and testing unit of claim 4, wherein said inverted tube has a triangular cross sectional configuration.

* * * * *